(12) United States Patent
Pfister

(10) Patent No.: US 9,220,472 B2
(45) Date of Patent: Dec. 29, 2015

(54) X-RAY C-ARM SYSTEM, FRAME FOR A FLAT-PANEL X-RAY DETECTOR OF AN X-RAY C-ARM SYSTEM AND METHOD FOR TECHNICAL SUPPORT OF TARGETING DURING PUNCTURING OF A PATIENT

(75) Inventor: Marcus Pfister, Bubenreuth (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 2756 days.

(21) Appl. No.: 11/786,787

(22) Filed: Apr. 12, 2007

(65) Prior Publication Data

US 2007/0255292 A1   Nov. 1, 2007

(30) Foreign Application Priority Data

Apr. 28, 2006 (DE) .................. 10 2006 020 403

(51) Int. Cl.
| | |
|---|---|
| *A61B 5/05* | (2006.01) |
| *A61B 6/00* | (2006.01) |
| *A61B 6/12* | (2006.01) |
| *A61B 19/00* | (2006.01) |

(52) U.S. Cl.
CPC .............. *A61B 6/5235* (2013.01); *A61B 6/12* (2013.01); *A61B 6/4233* (2013.01); *A61B 6/4441* (2013.01); *A61B 6/466* (2013.01); *A61B 19/201* (2013.01); *A61B 2019/5238* (2013.01)

(58) Field of Classification Search
CPC .................................................. A61B 19/201
USPC ........... 600/427; 378/20, 204, 205, 208, 209; 606/130; 5/601
See application file for complete search history.

(56) References Cited

U.S. PATENT DOCUMENTS

| | | | | |
|---|---|---|---|---|
| 3,702,935 | A * | 11/1972 | Carey et al. ............... | 378/189 |
| 4,485,815 | A * | 12/1984 | Amplatz et al. ........... | 606/185 |
| 4,576,175 | A * | 3/1986 | Epstein .................... | 600/461 |
| 4,875,478 | A * | 10/1989 | Chen ......................... | 600/429 |
| 5,056,523 | A * | 10/1991 | Hotchkiss et al. ........ | 600/427 |
| 5,515,416 | A * | 5/1996 | Siczek et al. ............. | 378/197 |
| 5,528,652 | A * | 6/1996 | Smith et al. .............. | 378/65 |
| 6,050,954 | A * | 4/2000 | Mittermeier ............. | 600/562 |
| 6,285,902 | B1 * | 9/2001 | Kienzle et al. ........... | 600/427 |
| 6,400,979 | B1 * | 6/2002 | Stoianovici et al. ..... | 600/427 |
| 2002/0082611 | A1 * | 6/2002 | Irie et al. ................. | 606/130 |
| 2002/0156360 | A1 * | 10/2002 | Ihamaki et al. ......... | 600/407 |
| 2003/0114862 | A1 * | 6/2003 | Chu et al. ................ | 606/130 |
| 2004/0015077 | A1 * | 1/2004 | Sati et al. ................ | 600/427 |
| 2005/0100129 | A1 * | 5/2005 | McKenna ................ | 378/37 |
| 2006/0036264 | A1 * | 2/2006 | Selover et al. .......... | 606/130 |
| 2006/0285638 | A1 | 12/2006 | Boese et al. | |

FOREIGN PATENT DOCUMENTS

DE        36 23 082 A1        1/1988

\* cited by examiner

*Primary Examiner* — Rajeev Siripurapu

(57) ABSTRACT

A puncturing needle holder is attached to a flat-panel x-ray detector such that it is visible in the x-ray image as a point. The point can involve the crossing area of two struts, which are attached to the flat-panel x-ray detector. Mappings are created in which on the one hand a region of the body to be punctured and on the other hand the point created by the puncturing needle holder are mapped by the x-ray images created with the flat-panel x-ray detector. The x-ray C-arm is moved until such time as precisely the puncturing needle holder is shown in the mapping so that it points to the region of the body to be punctured. Subsequent puncturing can then be carried out in a number of different ways.

16 Claims, 3 Drawing Sheets

X-RAY C-ARM SYSTEM, FRAME FOR A FLAT-PANEL X-RAY DETECTOR OF AN X-RAY C-ARM SYSTEM AND METHOD FOR TECHNICAL SUPPORT OF TARGETING DURING PUNCTURING OF A PATIENT

CROSS REFERENCE TO RELATED APPLICATIONS

This application claims priority of German application No. 10 2006 020 403.4 filed Apr. 28, 2006, which is incorporated by reference herein in its entirety.

FIELD OF THE INVENTION

The invention relates to an x-ray C-arm system with a rotatable (anglable) and tiltable C-arm, on which an x-ray source and a flat-panel x-ray detector with a flat surface are disposed. The invention also relates to a frame for attaching to the flat-panel x-ray detector of an x-ray C-arm. The invention also relates to a method for technical support of the targeting during puncturing of a patient.

BACKGROUND OF THE INVENTION

X-ray images, above all fluoroscopy images, have long been recorded to support interventional procedures, and this includes puncturing. The problem arising with puncturings is that very frequently the targets of the puncturing (such as gallstones or tumors) cannot be recognized at all on the x-ray images. The physician performing the treatment must thus basically use the skeleton of the patient for orientation. The practice of recording three-dimensional image data sets beforehand and registering these images with the x-ray system is known. The term registration means that the coordinates which apply for the three-dimensional 3D image data set are assigned to the coordinates of the x-ray system such that a mapping of the one coordinate system to the other coordinate system is defined (correct positional and dimensional assignment of the coordinates). The images from the one system, i.e. the images recorded beforehand, can then be assigned to the x-ray images recorded afterwards. The two-dimensionality of the x-ray images recorded afterwards requires them to be recorded from a specific perspective. Now, on the basis of the registration, i.e. as a result of the correct positional and dimensional assignment of the coordinates, a 2D image representation which assumes precisely this same perspective can now be created from the three-dimensional image data set. Then the two images, i.e. the recorded x-ray image and the computed 2D image can be overlaid. As with registration, the prior art includes a plurality of technologies for doing this. This method is preferably used for puncturings, with the three-dimensional image data being created with an imaging method in which the puncturing target is easily visible. The registration thus makes it possible for the puncturing target to be incorporated into the x-ray image that the physician records during the puncturing. This makes it possible for them to orient themselves during the puncturing.

The problem which arises with puncturing however is that the puncturing needle is almost one-dimensional. The needles are visible as line-shaped objects in the x-ray images. Not visible in this case is whether the needle in the direction perpendicular to the image plane is located in front of or behind the puncturing target, or whether it is actually pointing at the puncturing target. In a fluoroscopy image recorded from the side it is thus not possible to check in the plane perpendicular to the image plane whether the needle is located at the correct point.

It is not possible during a puncturing to record an image of the needle from above such that the image plane lies perpendicular to the extent of the needle, since then the physician's hands would come into the image which would involve a radiation risk to the physician.

A stereo x-ray apparatus is known from DE 36 23 082 A1 in which a puncturing needle is aligned in a holder before intervention into a patient. Sensors in the holder determine to position of the holder and calculate a target line of the puncturing needle from this. A target point at which the puncturing needle is currently pointing is then calculated for the stereo images. A target marking is then inserted in the stereo image at the location of the computed target point.

The arrangement disclosed in DE 36 23 082 A1 has however evidently not entered widespread use for a wide variety of reasons.

SUMMARY OF THE INVENTION

The object of the invention is to provide an option enabling technical support to be provided during puncturing for a physician enabling them to securely find the puncturing target.

This object is achieved by an x-ray C-arm system through a frame and through a method for technical support of the targeting during puncturing of a patient as claimed in the claims.

The invention is based on the knowledge that, although it is not possible to perform a mapping during the actual puncturing with the image plane perpendicular to the course of the puncturing needle because the hands of the physician would appear in the image, this can very well be done before the actual puncturing. The invention provides the option of defining the position of the puncturing needle before the actual puncturing and of subsequently retaining the targeting.

The inventive x-ray C-arm system is characterized by a puncturing needle holder being attached to the flat-panel x-ray detector which extends in a straight line perpendicular to the flat surface and can example be embodied as a straight tube. Directly accommodating the puncturing need in the puncturing needle holder on the flat-panel x-ray detector produces (and especially unlike in DE 36 23 082 A1) a direct relationship between the image perspective and the alignment of the puncturing needle. X-ray images which are recorded with the aid of the flat-panel x-ray detector, while the puncturing needle holder is gripping the puncturing needle, show precisely the view from the "insertion direction" of the needle. This therefore allows a target to be set in a defined manner.

Preferably the puncturing needle holder is accommodated at the crossing point of two intersecting struts, which are attached in parallel to the flat surface on the flat-panel x-ray detector and include material impermeable to x-rays or preferably are made entirely out of material impermeable to x-rays, for example metal. Since, as mentioned at the start, the puncturing needle can only be seen with difficulty in the x-ray image if the x-ray image is recorded at right angles to the puncturing needle, the effect of the two intersecting struts, which, since they consist of material impermeable to x-rays, are mapped in the x-ray image, is that of a type of cross-hair specifying the target of the puncturing needle. This greatly simplifies targeting.

Preferably the flat-panel x-ray detector is able to be moved relative to the C-arm in a direction perpendicular to its flat surface, as is the case with most x-ray C-arm systems of the prior art. In this case it is possible to attach the puncturing needle in the puncturing needle holder and, with the aid of the movement of the x-ray flat-panel detector, to perform the puncturing directly, with it being possible for the flat-panel x-ray detector to be moved far enough for the puncturing needle to be just touching the patient and for the physician to then move the puncturing needle further into the patient, and with it also being possible for the flat-panel x-ray detector to be moved further and thus for the needle to move in a precisely-targeted manner into the body of the patient.

In a preferred embodiment, which is used for an alternate puncturing preparation, the x-ray C-arm system includes an operation holder for the puncturing needle holder which is independent of the movement of the C-arm (meaning that it does not move together with the C-arm). The flat-panel x-ray detector is movable relative to the operation holder and/or the operation holder relative to the flat-panel x-ray detector (in more precise terms relative to the puncturing needle holder on the flat-panel x-ray detector). The puncturing needle holder can be attached to the operation holder and can be removed from the flat-panel x-ray detector, with the removal preferably being undertaken afterwards.

Thus it is possible to separate the puncturing needle which is held in the puncturing needle holder from the C-arm with the flat-panel x-ray detector. The operation holder can be arranged in the immediate vicinity of the patient. This makes it possible to take the puncturing needle directly out of the operation holder into the patient and to perform the actual targeting in a precisely defined manner. In such cases it should naturally be guaranteed that, when the puncturing needle holder is attached to the operation holder, its alignment and thereby the alignment of the puncturing needle does not change.

The operation holder can be height-adjustable and/or rotatable, with the "and" alternative including the ability of the operation holder to execute a combinable movement of rotation and height adjustment in one movement. It should be able to be latched into its position before the attachment of the puncturing needle holder, so that the targeting is not lost.

The inventive frame represents a means with which a conventional flat-panel x-ray detector of a x-ray C-arm system can be equipped differently in order to provide a x-ray C-arm system of the inventive type for executing the inventive method. Accordingly the shape of the frame is adapted to the shape of the flat-panel x-ray detector such that it can be attached to the flat-panel x-ray detector at a defined position. Located on the frame is at least one strut extending in the attached state parallel to the flat surface of the flat-panel x-ray detector and made of material impermeable to x-rays, to which a straight puncturing needle holder is attached (or can be attached and preferably also removed) such that it extends in the attached state of the frame perpendicular to the strut and thereby perpendicular to the flat surface of the flat-panel x-ray detector.

One strut is actually sufficient to attach the puncturing needle holder. If this is somewhat wider than the strut, the puncturing needle holder and thus the position of the puncturing needle can be detected in the x-ray image. Preferably the frame includes two struts made of material impermeable to x-rays however, which cross in a crossing area, and the puncturing needle holder is attached (or able to be attached) to the crossing area. In this case it is not necessary for the puncturing needle holder to be wider than the struts. The crossing area fixes the location of the puncturing needle holder. In the x-ray image the intersecting struts can be seen as a type of cross-hair, at the crossing point of which the target point also has to lie.

The inventive method for technical support of the targeting during puncturing of a patient includes the steps:
a) Provision of an inventive x-ray C-arm system, with a puncturing needle being able to be held in the puncturing needle holder right from the start,
b) Taking the patient into the x-ray C-arm system (usually on a patient table, with the flat-panel x-ray detector facing towards the patient),
c) Creating at least one mapping of an area of the patient's body to be punctured using the x-ray C-arm system, in which the puncturing needle holder and/or the puncturing needle is identified or is visible as a point object (by the above-mentioned cross-hair),
d) Repeating step c) for different rotation and tilt settings of the C-arm (i.e. moving the anglation and the tilt position of the C-arm) until the mapped point object lies precisely on a target point in the region of the body and
e) Making it possible to carry out the puncturing with the needle remaining on target.

The inventive method can be performed according to two alternatives, namely once with the inclusion of a registration, which was described at the start, and otherwise by dispensing with a registration. A registration is not necessary, if in the x-ray image of the region of the body to be punctured is sufficiently easy to see, if for example contrast media is provided there as a result of a previous measure. In this case the creation of the mapping merely involves recording an x-ray image.

A registration can also be undertaken, as is fundamentally known from the prior art, which is especially meaningful and actually necessary in the case in which the region of the body to be punctured cannot be seen or can only be seen with difficulty in the x-ray image. The method is in this case characterized in that the creating of the mapping(s) includes:
before step c) and preferably before step b) with a mapping process, in which the region of the body to be punctured can be represented, a three-dimensional image data set is obtained, of which the coordinate system is assigned through a registration to the coordinates of the C-arm, which are defined through its rotatabilty and tiltability, in a positionally and dimensionally correct manner,
then an x-ray image is recorded in each case, with the relevant coordinates of the C-arm being detected,
the coordinates of the 3D image data set assigned to the recorded coordinates are determined and a 2D image representation is created from the 3D image data set, which corresponds to the perspectives of the x-ray image which are defined by the coordinates of the C-arm system, and
the x-ray image is overlaid onto the 2D image representation and both are combined into the mapping, with from the x-ray image at least the point object and from the 3D image data set a representation of the region of the body to be punctured is to be seen in the mappings.

As already mentioned above, for the two previously-described alternatives of the method, either the puncturing needle with the flat-panel x-ray detector can be moved to the patient so that the physician can then subsequently insert the puncturing needle into the patient. (The puncturing needle can also be moved into the patient by moving the flat-panel x-ray detector, with this being left to the physician and their control of the flat-panel x-ray detector). Alternatively the puncturing needle holder is bought to the operation holder and/or the operation holder to the puncturing needle holder, attached to the operation holder while retaining its targeting defined in step d), and thus it is made possible for the physician to subsequently carry out the puncturing by guiding the needle in the puncturing needle holder through to the patient.

Preferably with the latter alternative the actual puncturing is provided with further support by fluoroscopy images, which are now however recorded from other perspectives. As a result the C-arm will be pivoted after the attachment of the puncturing needle to the operation holder (preferably by at least 90°), so that x-ray images in which the movement of the puncturing needle is shown can be recorded during the execution of the puncturing. The optimum benefit is then obtained from the removability of the puncturing needle holder from the flat-panel x-ray detector, which is thus in a fixed relationship to the needle when the first step is performed, so that the targeting can be defined and in the further step, i.e. for the actual puncturing, has the proven role as a supporting imaging system, as is known in the prior art.

BRIEF DESCRIPTION OF THE DRAWINGS

Preferred embodiments of the invention are described below with reference to the drawings, in which.

DETAILED DESCRIPTION OF THE INVENTION

Figure 1:
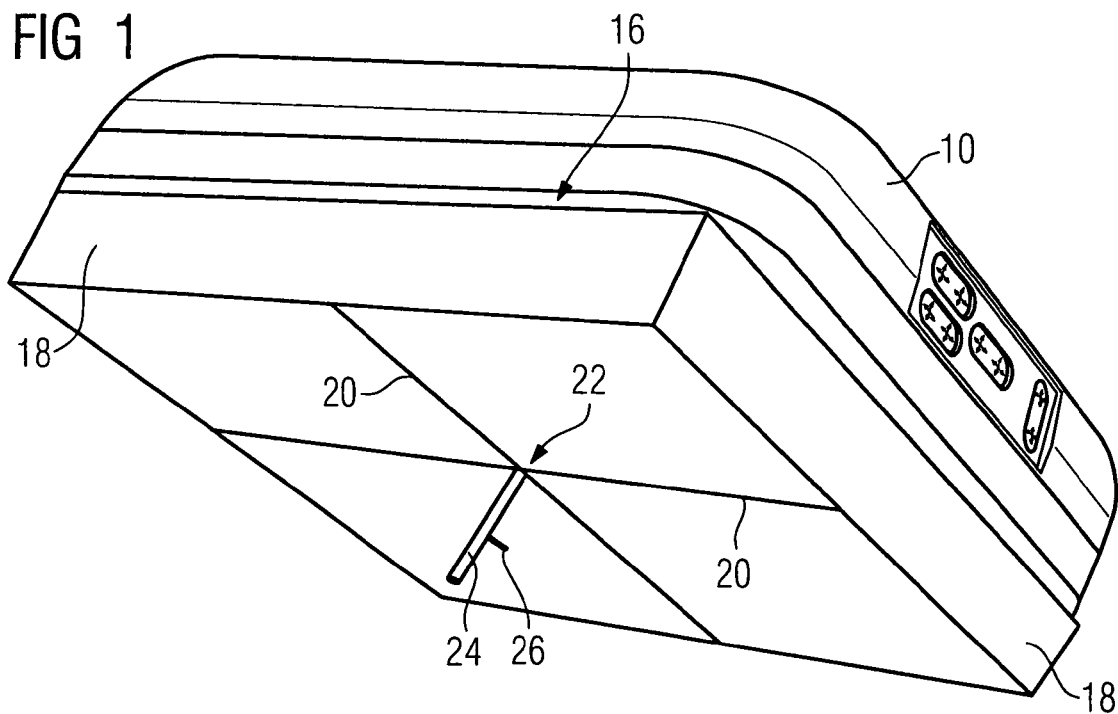
FIG. 1 shows a flat-panel x-ray detector equipped with an inventive frame.

Shown in FIG. 1 is a conventional flat-panel x-ray detector 10. Such a flat-panel x-ray detector 10 is attached to an x-ray C-arm system to an x-ray C-arm 12 (see FIG. 2). An x-ray tube 14 is attached on the opposite side as an x-ray source. As the term of the flat-panel x-ray detector already makes clear, this device has a flat surface.

In accordance with the invention a frame 16 with frame walls 18 is now attached to the flat-panel x-ray detector 10 (FIG. 1). The form of the frame 16 is adapted to the form of the flat-panel x-ray detector. Since the flat-panel x-ray detector has an essentially rectangular surface on the front, the frame 16 only has to be rectangular as well and have the same size as the flat-panel x-ray detector 10. The frame 16 is thus able to be attached to the flat-panel x-ray detector and is also shown attached in FIG. 1. Struts 20 extend in parallel to the frame walls 18 which intersect in a crossing area 22. The struts 20 are made of metal and are thus impermeable to x-rays. They extend in parallel to the plane of the flat-panel x-ray detector. Directly attached to the crossing area 22 is a puncturing needle holder 24. This is a tube of circular cross-section, in which an also circular puncturing needle can be inserted in a simple manner. A fixing pin 26 retains the needle in the tube. Instead of the fixing pin 26 use can be made of the close fit of the needle in the puncturing needle holder 24 to hold the needle.

The perpendicular movement of the rod-shaped puncturing needle holder 24 in relation to the flat surface of the flat-panel x-ray detector 10 means that the needle is not, as is almost always usual with x-ray images, to be seen as a line object but merely as a point shape. In the present case the puncturing needle holder is no larger than the dimensions of the crossing area 22, so that with correct perpendicular orientation of the puncturing needle holder 24, the puncturing needle holder is not to be seen at all in the x-ray image. In the x-ray images the crossing area 22 reflects information relating to the orientation of the needle. The x-ray images are in each case x-ray images as "seen by" the puncturing needle.

The crossing area 22 now only has to cover the region to be punctured in the x-ray images. The puncturing needle is then aligned directly onto the region to be punctured. In this case it is possible on the one hand for the region to be punctured to be sufficiently high-contrast for the recording of x-ray images with the aid of the x-ray tube 14 and of the flat-panel x-ray detector 10 to be enough to allow the region to be punctured to be targeted. Frequently or as a rule a previous three-dimensional mapping of the patient will be necessary by using another image mapping system (computer tomography, magnetic resonance device, dynamic computer tomography with the aid of which the organ to be punctured (usually gall bladder or liver) can be made visible. The three-dimensional image data set can also be recorded with the aid of the x-ray C-arm system. By registering the 3D image data set with the coordinates of the x-ray C-arm system it is possible to create two-dimensional images with the same perspective from the 3D image data set for the respective setting of the x-ray C-arm and thereby to the x-ray images made from this setting and to overlay the 2D image presentations from the 3D image data set with the x-ray images made. The region of the body to be punctured is then visible in the 3D image data set, in the x-ray images the cross which is formed by the struts 20 is visible, and the x-ray C-arm can be moved until the cross is aiming precisely at the region of the body to be punctured.

Subsequently further preparations can be made for the actual puncturing.

Figure 2:
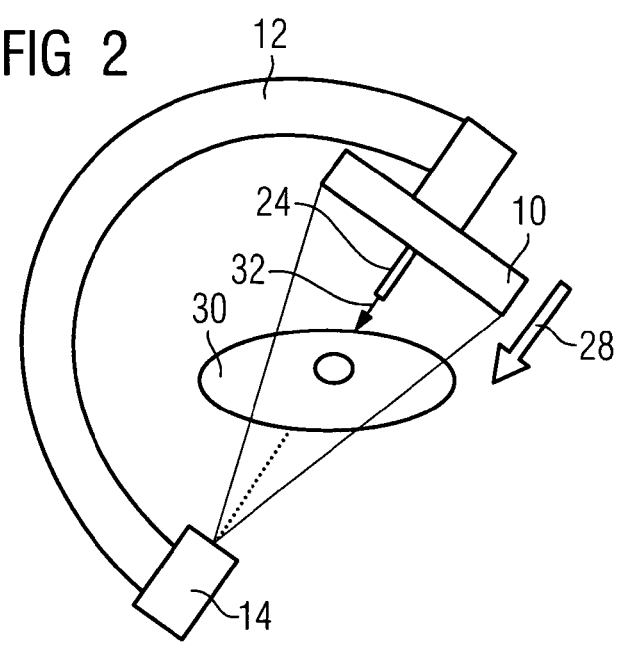
FIG. 2 shows the complete x-ray C-arm with the patient, positioned so as to allow a first type of puncturing, FIG. 3 and FIG. 4 which illustrate different steps of the execution of a puncturing, as made possible by a modified type of the x-ray C-arm system.

In an embodiment such as that illustrated in FIG. 2 the puncturing needle remains in the puncturing needle holder, once the C-arm 12 has been targeted. Conventional x-ray C-arms allow a movement of the flat-panel x-ray detector perpendicular to its (flat) surface, see arrow 28. In particular the flat-panel x-ray detector 10 can be moved in the direction of the patient 30. This means that the puncturing needle holder 24 and the position needle held within it also move in the direction of the patient 30 (see arrow 32). This movement can take place until such time as the puncturing needle has reached the patient 30. Subsequently the physician performing the treatment can carry out the actual puncturing by pushing in the needle further in the same direction. The manual intervention of the physician is not absolutely necessary. The flat-panel x-ray detector 10 can also move as shown by the arrow 28 further in the direction of the patient 30, so that the puncturing needle (which in this case must protrude sufficiently far out of the puncturing needle holder 24—not shown) penetrates into the patient 30, so that the actual puncturing is carried out by the movement of the flat-panel x-ray detector. If the puncturing needle has then penetrated sufficiently deeply into the patient, the flat-panel x-ray detector is withdrawn and the puncturing needle is available to the physician performing the treatment for further treatment steps.

Figure 3:
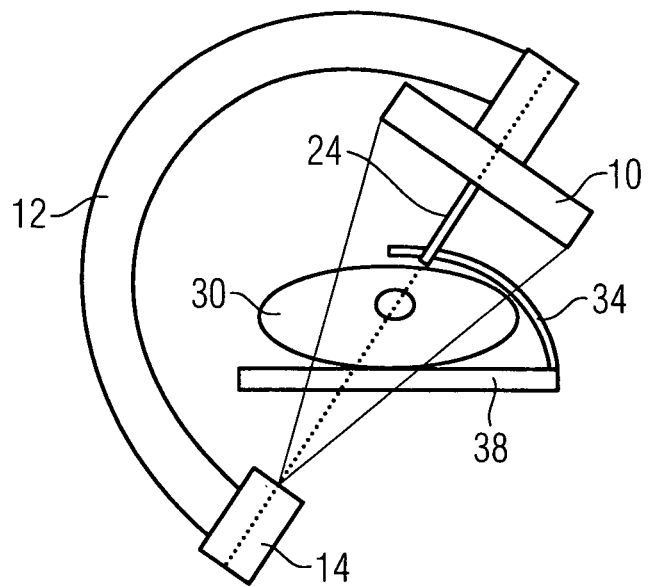
Figure 4:
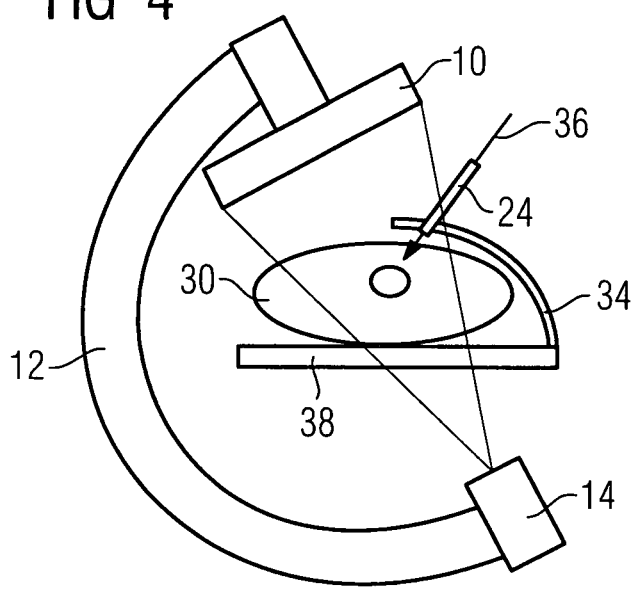

In an alternate embodiment of the invention an operation holder 34 is provided on the x-ray C-arm system, which, as shown, extends far enough for its free end (not specially indicated) to move into the vicinity of the puncturing needle holder 24 and preferably to move the latter. The free end of the operation holder 34 can be embodied in the shape of a fork, with the operation holder 34 then preferably being moved so that the fork encloses the puncturing needle holder 24. It is then possible, to initially bring the puncturing needle holder 24 into the target position (as described above), to attach it to the operation holder 34 and subsequently to release it from the flat-panel x-ray detector 10. The transition point of the puncturing needle holder 24 from the flat-panel x-ray detector 10 to the operation holder 34 is shown in FIG. 3 and FIG. 4 shows that subsequently the x-ray C-arm 12 and thereby the flat-panel x-ray detector 10 are moved. The puncturing needle can actually already be held in the puncturing needle holder 24. Preferably however it is only pushed into the latter after the release of the puncturing needle holder 24 from the flat-panel x-ray detector (shown in FIG. 4: the needle is labeled with the reference number 36). If it was guaranteed that the puncturing needle holder has retained its targeting on transition from the flat-panel x-ray detector 10 to the operation holder 34, the puncturing needle 36 is pointing in the right direction. It is then possible for the physician to precisely target the puncturing needle 36, via the puncturing needle holder 24, in the patient 30 and to carry out the actual puncturing. By moving the C-arm 12 it is possible to record fluoroscopy images from other perspectives during the puncturing, in which the needle is then shown as a line, further supporting the physician in his treatment.

The operation holder 34 is shown in the diagram attached to the patient table 38, on which the patient 30 lies. More detailed illustrations of the operation holder 34 can be found in FIGS. 5 to 7, which show the operation holder with the patient 30 on the patient table 38 from three perspectives at right angles to one another (from the front, from the side and from the top).

Figure 5:
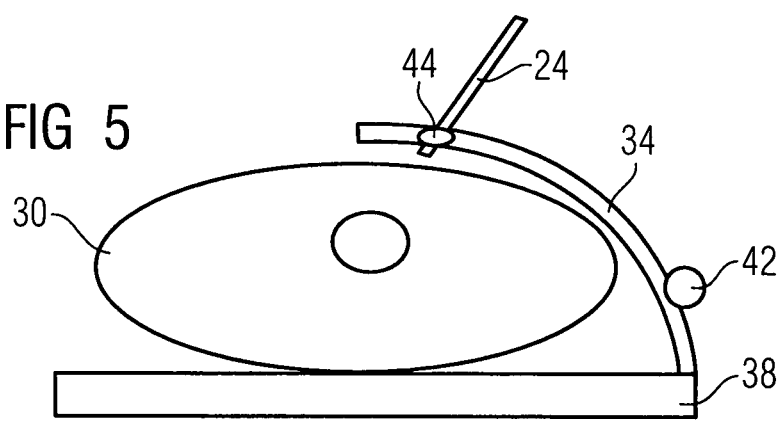
FIG. 5 to FIG. 7 illustrate views of the operation holder used in an embodiment of the invention.
Figure 6:
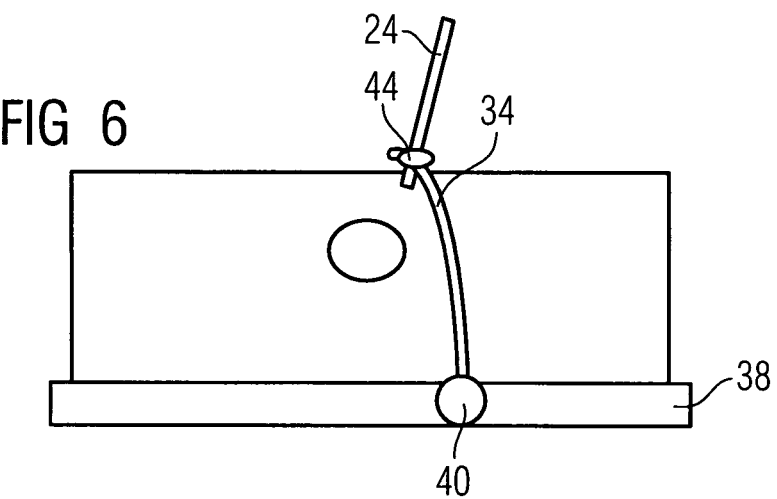
Figure 7:
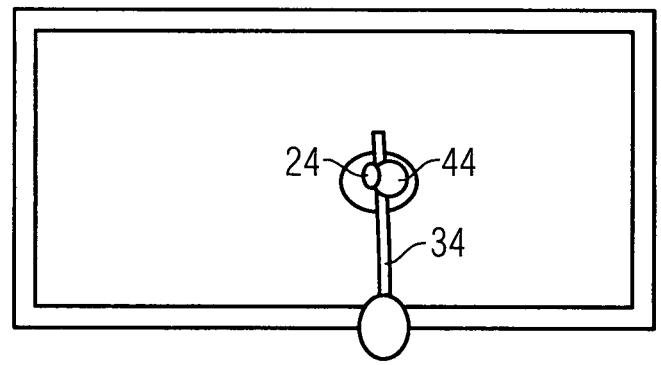

The operation holder 34 can be rotated around an axis perpendicular to the patient table 38, see the joint 40 in FIG. 6 which symbolizes this. It can be moved up and down at right angles to this axis (symbolized by the joint 42 in FIG. 5). Shown in FIGS. 5 to 7 is the operation holder 34 with the puncturing needle holder 24 attached to it. The holder can be attached in any way and the only guarantee required is that the targeting is retained. A clamping screw 44 is shown symbolically.

The invention provides a practical auxiliary apparatus for an x-ray C-arm system, namely the frame 16 with the walls 18, the struts 20 and the puncturing needle holder 26, through which an x-ray C-arm system can be equipped before a puncturing is carried out so that the puncturing can be supported technically in a manner that was not previously known. The physician is especially supported technically during the actual puncturing to allow precisely targeted and safe puncturing to be undertaken.

The invention claimed is:

1. An X-ray C-arm system, comprising:
an x-ray source that emits x-rays;
a flat-panel x-ray detector with a flat surface;
a rotatable and tiltable C-arm on which the x-ray source and the flat-panel x-ray detector are disposed; and
a puncturing needle holder that is arranged on the flat-panel x-ray detector and extends in a straight line perpendicular to the flat surface and in a direction from the flat surface to the x-ray source;
wherein the puncturing needle holder is attached in a cross area of two intersecting struts that extend parallel to the flat surface and wherein the struts are attached to the flat-panel x-ray detector and impermeable to the x-rays.

2. The x-ray C-arm system as claimed in claim 1, further comprising a puncturing needle configured to be inserted within the puncturing needle holder.

3. The x-ray C-arm system as claimed in claim 1, wherein the puncturing needle holder is a tube having a circular cross-section in which a puncturing needle having a circular cross-section is configured to be inserted.

4. The x-ray C-arm system as claimed in claim 3, further comprising a fixing pin configured to retain the puncturing needle within the tube.

5. The x-ray C-arm system as claimed in claim 4, wherein the fixing pin is oriented orthogonal to the puncturing needle holder.

6. The x-ray C-arm system as claimed in claim 1, further comprising an operation holder that is configured not to move with the C-arm, said operation holder including a free arm configured to extend into a vicinity of the puncturing needle holder, said free arm configured to move the puncturing needle holder.

7. The x-ray C-arm system as claimed in claim 6, wherein the flat-panel x-ray detector is configured to move to the operation holder or the operation holder is configured to move to the flat-panel x-ray detector.

8. The x-ray C-arm system as claimed in claim 7, wherein the puncturing needle holder is configured to attach to the free arm of the operation holder and subsequently configured to be removed from the flat-panel x-ray detector.

9. The x-ray C-arm system as claimed in claim 6, wherein the operation holder is attached to a patient table and is configured to rotate around an axis perpendicular to the patient table, said operator holder is height-adjustable and is latched into a position before being attached to the puncturing needle holder.

10. The x-ray C-arm system as claimed in claim 1, wherein the struts comprise a metal material.

11. The x-ray C-arm system as claimed in claim 1, further comprising:
a frame with frame walls attached to the flat-panel x-ray detector;
wherein a form of the frame is adapted to a form of the flat-pane x-ray detector;
and wherein the frame has a same size as the flat-panel x-ray detector.

12. The x-ray C-arm system as claimed in claim 1, wherein a dimension of the puncturing needle holder to intersect the cross area is less than a dimension of the cross area intersected by the puncturing needle holder.

13. The x-ray C-arm system as claimed in claim 6, wherein said free arm is configured to attach to the puncturing needle holder.

14. The x-ray C-arm system as claimed in claim 13, wherein said operation holder further includes an end opposite to the free arm which is attached to a patient table.

15. The x-ray C-arm system as claimed in claim 13, wherein said free end is a fork and wherein the operation holder is configured to be moved such that the fork partially encloses the puncturing needle holder.

16. An X-ray C-arm system, comprising:
an x-ray source that emits x-rays;
a flat-panel x-ray detector with a flat surface;
a rotatable and tiltable C-arm on which the x-ray source and the flat-panel x-ray detector are disposed; and
a puncturing needle holder that is arranged on the flat-panel x-ray detector and extends in a straight line perpendicular to the flat surface and in a direction from the flat surface to the x-ray source;
wherein the flat-panel x-ray detector is configured to move relative to the C-arm in a direction perpendicular to the flat surface.

* * * * *